United States Patent [19]

Holmes et al.

[11] Patent Number: 4,477,654
[45] Date of Patent: Oct. 16, 1984

[54] 3-HYDROXYBUTYRATE POLYMERS

[75] Inventors: Paul A. Holmes, Middlesbrough; Stephen H. Collins, Thirsk; Leonard F. Wright, Eaglescliffe, all of England

[73] Assignee: Imperial Chemical Industries PLC, London, England

[21] Appl. No.: 393,407

[22] Filed: Jun. 29, 1982

Related U.S. Application Data

[63] Continuation-in-part of Ser. No. 319,673, Nov. 9, 1981, abandoned.

[30] Foreign Application Priority Data

Jul. 7, 1981 [GB] United Kingdom ............... 8120991
May 12, 1982 [GB] United Kingdom ............... 8213697

[51] Int. Cl.$^3$ ............................................. C08G 63/06
[52] U.S. Cl. ................................... 528/361; 435/135; 435/829; 435/872; 106/287.24
[58] Field of Search ............... 528/361; 435/135, 829, 435/872

[56] References Cited

U.S. PATENT DOCUMENTS

| | | | |
|---|---|---|---|
| 3,275,610 | 9/1966 | Coty | 528/361 X |
| 3,579,549 | 5/1971 | Stockmann et al. | 260/410.9 R |
| 4,101,533 | 7/1978 | Lafferty et al. | 528/361 X |
| 4,138,291 | 2/1979 | Lafferty | 435/29 X |
| 4,324,880 | 4/1982 | Dhein et al. | 528/361 X |

OTHER PUBLICATIONS

Wallen et al., "Biopolymers of Activated Sludge", Environmental Science & Technology 6, 161–164, (1972).
Wallen et al., "Poly-β-hydroxyalkanoate from Activated Sludge", Environmental Science & Technology 8, 576–579, (1974).
Davis, "Cellular Lipids of a Nocardia Grown on Propane and n-Butane", Applied Microbiology 12, 301–304, (1964).
Marchessault et al., "Physical Properties of Poly-β-hydroxyvalerate", IUPAC, Macro Florence 1980, Int'l. Symposium on Macromolecules, Preprints, vol. 2, 272–276, (1980).

*Primary Examiner*—Earl A. Nielsen
*Attorney, Agent, or Firm*—Cushman, Darby & Cushman

[57] ABSTRACT

High molecular weight copolymers containing 3-hydroxybutyrate residue, i.e. units of the formula $$-O.CH(CH_3).CH_2.CO-$$

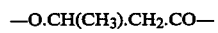

and up to 50 mole % of residues of other hydroxy acids, viz units of the formula $$-O.CR^1R^2.(CR^3R^4)_n.CO-$$

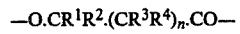

where n is 0 or an integer and, if n=1 and $R^2$, $R^3$, and $R^4$=H, $R^1$ is not methyl.

The copolymers are made microbiologically: for part of the cultivation the micro-organism is under conditions such that polymer is accumulated, e.g. by limitation of a nutrient, e.g. nitrogen source, required for growth but not polyester accumulation. For at least part of this period of polymer accumulation the substrate is an acid or a derivative thereof that gives the comonomer units. Proprionic acid, which gives polymers where n=1, $R^2=R^3=R^4=H$ and $R^1=C_2H_5$, is the preferred acid.

21 Claims, No Drawings

3-HYDROXYBUTYRATE POLYMERS

This application is a continuation-in-part of our application Ser. No. 319,673 filed Nov. 9, 1981, now abandoned.

This invention relates to 3-hydroxybutyrate polymers hereinafter referred to as PHB.

PHB is accumulated by various micro-organisms, principally bacteria, as an energy reserve material as granules within the microbial cells.

PHB extracted from such cells is a thermoplastic polyester of the repeat structure

—O.CH(CH$_3$).CH$_2$.CO— that rapidly crystallises to a relatively high level e.g. of the order of 70% or more. This crystallisation behaviour is often disadvantageous when the polymer is to be used as, for example, a moulding material.

We have found that the crystallisation of PHB can be modified by incorporation of units of a dissimilar monomer into the polymer chain. Thus a minor proportion of comonomer units may be introduced into the polymer chain by cultivation of the micro-organism under certain conditions in the presence of certain organic acids. One example of such an acid is propionic acid.

Although we do not wish to be bound by the following theory, it is thought that the metabolic pathway leading to such copolymers is as follows, in which CoASH is unesterified Coenzyme A, (So CH$_3$.CO.S.-CoA is the acetyl thioester of Coenzyme A and is more commonly termed acetyl CoA), and NADP is nicotinamide adenine dinucleotide phosphate in the oxidised state. NADPH$_2$ is reduced NADP.

It is believed that, in the biosynthesis of PHB by a micro-organism the first step is the synthesis of acetyl CoA. This can be formed, for example, from Coenzyme A and acetate, or by the decarboxylation of pyruvate, which is a product of the glycolysis of carbohydrates, or which can be formed by decarboxylation of oxaloacetate, the latter being a member of the tricarboxylic acid, TCA, cycle, otherwise known as the Krebs cycle.

Thus with acetate as the source of acetyl CoA, the PHB is produced by a metabolic pathway involving the reactions:

1. CH$_3$.CO.O$^-$ + CoA.SH $\xrightarrow{\text{thiokinase}}$

CH$_3$.CO.S.CoA + OH$^-$ 2. 2CH$_3$.CO.S.CoA $\xrightarrow{\beta\text{-ketothiolase}}$ CH$_3$.CO.CH$_2$CO.S.CoA + CoA.SH 3. CH$_3$.CO.CH$_2$.CO.S.CoA + NADPH$_2$ $\xrightarrow{\text{reductase}}$ CH$_3$.CHOH.CH$_2$.CO.S.CoA + NADP
    3-hydroxybutyryl CoA 4. CH$_3$.CHOH.CH$_2$.CO.S.CoA $\xrightarrow{\text{polymerase}}$ —O.CH(CH$_3$).CH$_2$.CO— + CoASH
    repeat unit in polymer Thus reaction 4 adds a —O.CH(CH$_3$).CH$_2$.CO— unit to a growing polymer chain.

Because of lack of specificity of the enzymes involved, with propionic acid, the corresponding pathway is thought to be:

1a. CH$_3$.CH$_2$.COO$^-$ + CoA.SH→CH$_3$.CH$_2$.CO.S.-CoA + OH$^-$

2a. CH$_3$.CH$_2$.CO.S.CoA + CH$_3$.CO.S.-CoA→CH$_3$.CH$_2$.CO.CH$_2$.CO.S.CoA + CoA.SH

3a. CH$_3$.CH$_2$.CO.CH$_2$.COS.CoA +- NADPH$_2$→CH$_3$.CH$_2$.CHOH.CH$_2$.CO.SCoA +- NADP

4a. CH$_3$.CH$_2$.CHOH.CH$_2$.CO.S.-CoA→—O.CH(C$_2$H$_5$).CH$_2$.CO—+CoA.SH i.e. repeat units having a pendant ethyl group are introduced into the polymer chain: in contrast PHB has pendant methyl groups.

Certain polymers containing 3-hydroxybutyrate units, i.e.

—O.CH(CH$_3$).CH$_2$.CO— units, together with other units have been described in the literature.

Thus polymers exhibiting an infra-red band said to be indicative of ethylenic unsaturation are described by Davis in "Applied Microbiology" 12 (1964) pages 301–304. These polymers which are said by Davis to be copolymers containing 3-hydroxybutyrate units and 3-hydroxy-2-butenoate units, i.e. units of the formula

—O.C(CH$_3$)═CH.CO— were prepared by cultivating Nocardia on n-butane.

Also Wallen et al describe in "Environmental Science and Technology" 6 (1972) pages 161–164 and 8 (1974) pages 576–579 a polymer melting at 97°–100° C. (after repeated washing) isolated from activated sludges and containing 3-hydroxybutyrate units and 3-hydroxyvalerate units, i.e.

—O.CH(C$_2$H$_5$).CH$_2$.CO— units in the ratio of 1:5. The polymer thus contains only about 17% of 3-hydroxbutyrate units. Marchessault et al report in "IUPAC Macro Florence 1980 International Symposium on Macromolecules Preprints" 2 (1980) pages 272–275 a study of this polymer and confirmed that it contained mainly 3-hydroxyvalerate units.

U.S. Pat. No. 3,275,610 describes the microbiological production of polyesters by cultivating certain micro-organisms, especially *Nocardia salmonicolor*, on carboxylic acids containing 4 carbon atoms. In Examples 2 and 3, where the acids were 3-butenoic and 2-hydroxybutyric acids respectively, the polymers appear, from the quoted melting points of the order of 178°–184° C., to be poly(3-hydroxybutyrate). In Example 1 however, wherein 2-methyl acrylic acid, i.e. methacrylic acid, was employed the polymer produced is unidentified but is described as having a melting point of 215°–220° C. and as being soluble in methyl ethyl ketone. In contrast thereto, copolymers in accordance with the present invention, containing predominantly 3-hydroxybutyrate residues, have melting points below 180° C. and are insoluble in cold methyl ethyl ketone.

When PHB-accumulating micro-organisms are aerobically cultured on a suitable substrate, i.e. a source of energy and carbon, they reproduce until one or more of the essential requirements for reproduction is exhausted. This reproduction of the micro-organism is hereinafter referred to as growth. Upon exhaustion of an essential growth requirement, further growth occurs only to a very limited extent, if at all, but, providing the substrate is not exhausted, PHB may be accumulated by the micro-organism.

With some micro-organisms, even in the absence of a PHB-inducing constraint such as a limitation on one or more of the essential growth requirements, PHB may also be accumulated while growth of the micro-organism is taking place: however, except in the case of micro-organisms that produce PHB constitutively, the amount of PHB so accumulated is generally small and typically is less than about 10% by weight of the cells produced. Thus when grown in batch culture, the micro-organisms that do not produce PHB constitutively, will grow, with little or no PHB accumulation, until one or more of the essential requirements for growth becomes exhausted, and then the micro-organism synthesises PHB. In order to produce copolymers it is therefore necessary to use the acid (or a derivative thereof) that is to give rise to the copolymer units other than 3-hydroxybutyrate units as at least part of the substrate present during the period when polymer is accumulated. The acid, or derivative thereof, that gives rise to the copolymer units other than 3-hydroxybutyrate units is herein termed the comonomer component of the substrate.

When the cultivation conditions are such that the polyester, e.g. PHB, is not being accumulated to any significant extent, the comonomer component of the substrate will often be metabolised by the micro-organism by other pathways leading to e.g. acetyl CoA or to a member of the TCA cycle, and so copolymers will not be produced. Thus, as an example, propionic acid can be metabolised by micro-organisms, in the absence of any growth limitation, via propionyl CoA, with the incorporation of carbon dioxide to methyl malonyl CoA, and thence to succinate, a member of the TCA cycle.

Metabolism of the comonomer component of the substrate by such other pathways may also occur when using micro-organisms that produce PHB constitutively. Hence we prefer, even when using constitutive PHB-containing micro-organisms to cause the polymer to be accumulated by cultivation of the micro-organism under conditions wherein the amount of one or more of the essential requirements for growth, but not PHB accumulation, is limited. Even when cultivating the micro-organism under conditions where there is a restriction of an essential requirement for growth, so that polymer is accumulated by the micro-organism, some of the comonomer component of the substrate may be metabolised by pathways leading to acetyl CoA or a member of the TCA cycle. This enables the micro-organism to synthesise 3-hydroxybutyrate units for incorporation into the copolymer as well as the dissimilar copolymer units, even if the comonomer component is the sole substrate during the polymer accumulation stage. Also, as indicated by the metabolic pathway suggested above for the production of 3-hydroxyvalerate units from propionate, one step, reaction 2a, involves the reaction of propionyl CoA with acetyl CoA. Hence if propionate is the sole substrate, some of the propionate is metabolised to acetyl CoA in order that 3-hydroxyvalerate units can be produced.

In addition to the metabolic pathways shown above, leading to 3-hydroxyvalerate units in the copolymer, other reactions can occur with various other materials as the comonomer component of the substrate.

For example it is possible that other hydroxy substituted carboxylic acids, if not metabolised by other routes leading to e.g. acetyl or propionyl CoA, could in some cases be incorporated directly by the polymerase into the polymer, e.g.

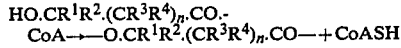

where n is 0 or an integer and $R^1$, $R^2$, $R^3$, $R^4$, which may be the same or different, are selected from hydrocarbon radicals, such as alkyl, aralkyl, aryl, or alkaryl radicals; halo- and hydroxy-substituted hydrocarbon radicals; hydroxy radicals; halogen atoms; and hydrogen atoms. Of course where $n=1$ and $R^2=R^3=R^4=$hydrogen, if $R^1$ is methyl the hydroxycarboxylic acid is 3-hydroxybutyric acid which of course will be directly assimilated to give 3-hydroxybutyrate units.

Preferably the groups $R^1$, $R^2$, $R^3$ and $R^4$ each contain less than 4 carbon atoms. Generally at least one of the groups $R^1$, $R^2$, $R^3$ and $R^4$ is hydrogen. n is preferably 0, 1 or 2.

Such hydroxy-carboxylic acids may be added as such (as part, or all, of the comonomer component of the substrate) or may be synthesised by the micro-organism from other comonomer component materials.

In particular we have found that acids such as acrylic, 3-chloropropionic, and 3-hydroxypropionic acids may give rise to polymers containing 3-hydroxybutyrate units and other units. In some cases all these other units are 3-hydroxyvalerate units while in other cases, the other units which are hereinafter termed units A and which may occur in conjunction with 3-hydroxyvalerate units, are characterised by proton and $^{13}C$ nuclear magnetic resonance spectra exhibiting, inter alia, (i) a proton NMR triplet at 4.3 ppm, and (ii) $^{13}C$ NMR peaks at 59.89 and 33.83 ppm (relative to a tetramethyl silane standard).

From these NMR data it is believed that these units are 3-hydroxypropionate units (i.e. $n=1$; $R^1=R^2=R^3=R^4=H$).

The copolymers may also contain 4-hydroxyvalerate units i.e. $n=2$; $R^1=CH_3$; $R^2=R^3=R^4=H$.

3-Hydroxypropionate and/or 4-hydroxyvalerate units could result from the intermediates $CH_2OH.CH_2.CO.S.CoA$ and $CH_3.CHOH.CH_2.CO.SCoA$. The former could be formed from 3-hydroxypropionate and CoA.SH. In addition to being supplied as such, 3-hydroxypropionate could be formed by the hydration of acrylate:

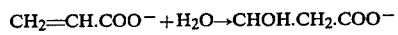

or by the hydrolysis of 3-chloropropionate

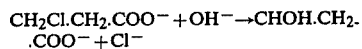

4-hydroxyvaleryl CoA could be derived from the condensation of acetyl CoA and acrylyl CoA followed by reduction, i.e.

CH$_3$.CO.S.CoA+CH$_2$=CH.CO.S.CoA→CH$_3$.CO.CH=CH.CO.S.CoA+CoA.SH

CH$_3$.CO.CH=CH.CO.S.CoA+2NADPH$_2$→CH$_3$.CHOH.CH$_2$.CH$_2$.CO.S.CoA+2NADP

Similarly 4-hydroxyvaleryl CoA could be produced from 3-hydroxy-, or 3-chloro-propionate by reactions involving condensation with acetyl CoA, reduction, and dehydration (with an intermediate hydrolysis step in the case of 3-chloropropionate).

By the process of the present invention it is therefore possible to obtain copolymers containing 3-hydroxybutyrate units.

—O.CH(CH$_3$).CH$_2$.CO.—    I together with units of the formula

—O.CR$^1$R$^2$.(CR$^3$R$^4$)$_n$.CO—    II where n is 0 or an integer and R$^1$, R$^2$, R$^3$, and R$^4$ are each selected from hydrocarbon radicals, such as alkyl, aralkyl, aryl, or alkaryl radicals; halo- and hydroxy-substituted hydrocarbon radicals; hydroxy radicals; halogen atoms; and hydrogen atoms, provided that, where n is 1, if R$^2$, R$^3$ and R$^4$ are each hydrogen atoms, R$^1$ is not methyl.

Preferably the groups R$^1$, R$^2$, R$^3$ and R$^4$ each contain less than 4 carbon atoms. Generally at least one of the groups R$^1$, R$^2$, R$^3$ and R$^4$ is hydrogen. Preferably n is 0, 1 or 2.

The copolymers may contain more than one type of unit II.

Preferably in at least some of the units II n=1, R$^2$=R$^3$=R$^4$=H and R$^1$=ethyl.

To be of any practical use as plastics materials, the polymers should have a weight average molecular weight, (Mw), above 10,000 e.g. as measured by gel permeation chromatography.

The proportion of repeat units II in the copolymer is preferably between 0.1 and 50, particularly 1 to 40, mole percent of the total repeat units in the copolymer. In some cases the polymer produced by the micro-organism may be a blend of a homopolymer of repeat units I with a copolymer containing repeat units I and II. In this case the overall proportion of repeat units II in the polymer is preferably between 0.1 and 50 mole percent of the total repeat units. Most preferably the proportion of repeat units II in the polymer is between 3 and 30 mole %.

In order to obtain a significant proportion of comonomer units II, the amount of combined carbon in the comonomer component of the substrate should be at least 2%, preferably at least 10% by weight of the total combined carbon in the substrate present during the period when the cultivation conditions are such that polymer is being accumulated by the micro-organism.

During this period, we prefer that the comonomer component is the only carboxylic acid (or derivative thereof) present in the substrate, although in some cases acetate may also be present.

According to the present invention we therefore provide a process for the production of a thermoplastic polyester wherein a micro-organism that is capable of accumulating a polyester is cultivated in an aqueous medium on a water soluble assimilable carbon containing substrate with at least part of the cultivation being conducted under conditions causing polyester to be accumulated by the micro-organism characterised in that, at least during part of the period when polyester is being accumulated, the substrate comprises an organic acid, or derivative thereof, that is metabolisable by said micro-organism under said polyester accumulating conditions, to a polyester other than one composed solely of —O.CH(CH$_3$).CH$_2$.CO— repeat units, the amount of combined carbon in said acid, or derivative thereof, constituting at least 2% by weight of the total combined carbon in the substrate present throughout said period.

The concentration of the comonomer component in the aqueous medium should be above 0.05 g/l and will preferably be at a level between 0.1 and 5 g/l. It will therefore be appreciated that the water solubility of the comonomer component should be above 0.05 g/l and sufficient to provide the desired level of the comonomer component concentration at the cultivation temperature.

The comonomer component may be the acid itself or a salt, ester (including a lactone in the case of a hydroxy substituted acid), anhydride, amide or halide.

As mentioned hereinbefore, it is preferred that at least part of the cultivation is conducted under conditions of limitation of an essential requirement for growth but not polyester accumulation. The most convenient growth requirement limitation is limitation of nitrogen. For this reason, where nitrogen limitation is employed, the substrate is preferably nitrogen free and so amides are less preferred substrates.

Acids that can be used to produce copolymers should be those that do not give rise only to repeat units I, when the cultivation is in the polymer accumulating stage. Unsuitable acids therefore include acetic and 3-hydroxybutyric acids, members of the TCA cycle, and acids giving only acetyl CoA and/or a member of the TCA cycle when the cultivation is in the polymer accumulating stage. Thus unsuitable acids also include phosphoglyceric, pyruvic, citric, isocitric, α-ketoglutaric, succinic, fumaric, maleic, malic, oxalacetic, oxalosuccinic, aconitic, and methyl malonic, acids. Amino acids are likewise unsuitable. Other acids that have been found not to give copolymers include formic, butyric, phenyl acetic, benzoic, chloroacetic, 2-chloropropionic, 3-hydroxybutyric, 4-hydroxybutyric, 2-chlorobutyric, 2-methylacrylic, 2,3-dimethylacrylic, 3,3-dimethylacrylic, lactic, glyoxylic and glycolic acids.

Acids that have been found to give copolymers include propionic, 3-hydroxypropionic, 3-chloropropionic, 3-ethoxypropionic, 2-hydroxybutyric, isobutyric, and acrylic acids. Other acids that could be used include higher saturated carboxylic acids containing an odd number of carbon atoms, e.g. valeric and heptanoic acids; pivalic acid; and substituted propenoic acids, e.g. 2- and 3-chloropropenoic acids.

As mentioned hereinbefore, in some cases the micro-organism may perform further reactions on the acid: thus isobutyric acid would be expected to give repeat units II in which n is 1, R$^2$=R$^3$=R$^4$=H, and R$^1$ is isopropyl. In fact repeat units of the type II wherein n is 1, R$^2$=R$^3$=R$^4$=H, and R$^1$ is ethyl are found indicating that the micro-organism here substitutes hydrogen for a methyl group during the metabolic pathway to the copolymer.

Preferred acids that can give rise to copolymers are propionic, isobutyric, and acrylic acids. Suitable derivatives of such acids include the alkali metal salts thereof and the lower alkyl esters (in which the alkyl group contains 1 to 4 carbon atoms). Particularly suitable esters include methyl, ethyl, isopropyl, propyl, butyl and isobutyl propionates; methyl and ethyl isobutyrates; and methyl and ethyl acrylates.

Mixtures of copolymers forming acids (or derivatives thereof) may be used as the comonomer component of the substrate. For example interesting results have been obtained using a mixture of propionic and acrylic acids.

As indicated above, it is preferred, even when using a micro-organism that produces PHB constitutively, to conduct the period of cultivation of the micro-organism where polyester is being accumulated under conditions of limitation of a nutrient required for growth but not polyester accumulation.

In addition to the substrate and oxygen (which is generally supplied by injecting air into the aqueous medium in the fermenter), various nutrient salts are required to enable the micro-organism to grow. Thus sources of the following elements in assimilable form, normally as water soluble salts, are generally required: nitrogen, phosphorus, sulphur, potassium, sodium, magnesium, calcium, and iron, together with traces of elements such as manganese, zinc and copper. While it may be possible to induce polyester accumulation by restricting the supply of oxygen to the fermenter, it is preferred to restrict the amount of one or more of the nutrient salts. The most practical elements to limit are nitrogen, phosphorus, or, less preferably, magnesium, sulphur or potassium. Of these it is most preferred to restrict the amount of nitrogen (which is conveniently supplied as an ammonium salt). The amount of assimilable nitrogen required is about 8-15% by weight of the desired weight of cells less accumulated polyester.

The fermentation is preferably conducted so that the dry weight of the polyester-containing cells is at least 5 g per liter of aqueous medium. Hence if, for example, it is desired to produce 10 g per liter of PHB-containing cells having a PHB content of 40% by weight, the amount of the essential nutrient fed to the fermenter that is used to limit the amount of cell growth must be that required to support the growth of 6 g per liter of cells containing no PHB: thus, if nitrogen is employed as the growth limiting nutrient, since the nitrogen content of PHB free bacterial cells is about 8-15% by weight, the amount of assimilable nitrogen required would be between about 0.5 and 0.9 g per liter, e.g. about 0.6 to 1.2 g of ammonium ions per liter.

The fermentation may be conducted under the conditions e.g. pH, temperature, and degree of aeration (unless oxygen is utilised as the limiting nutrient) conventionally used for the micro-organism. Likewise the amounts of nutrient salts (other that the growth limiting nutrient whose amount may be determined following the considerations outlined hereinbefore) employed may be those normally used for growth of the micro-organism.

The micro-organism is preferably grown to a certain desired weight by cultivation in the presence of sufficient of the nutrient required for growth that is to be restricted in the polymer accumulation stage on a readily metabolisable substrate, such as a carbohydrate, and then cultivated under conditions of growth requirement restriction to cause the polymer accumulation. In some cases the substrate for at least part, and in some cases all, of the growth stage may be the acid (or derivative thereof) that gives rise to the copolymer repeat units II in the polymer accumulation stage.

The fermentation may be performed as a batch fermentation in which case polymer accumulation will occur as the amount of the nutrient that is required for growth but not polymer accumulation becomes depleted, i.e. exhausted. Alternatively the fermentation may be conducted as a continuous process wherein aqueous medium containing the bacterial cells is removed, continuously or intermittently, from the fermentation vessel at a rate corresponding to the rate of addition of fresh aqueous medium and substrate thereto. It is preferred that the amount of the nutrient that is restricted that is fed to the fermentation vessel is such that the aqueous medium removed from the vessel contains little or none of that nutrient, and the aqueous medium removed from the vessel is then fed to a second fermentation vessel, operated either in batch or, preferably, continuous fashion wherein polymer accumulation is caused to take place by continuing the aerobic cultivation with the addition of a fresh quantity of substrate comprising the comonomer component. While additional quantities of substrate and nutrient salts may be added in this further fermentation step, since further growth is generally not desired, little or no further quantity of the nutrient utilised to limit growth should be added. It will however be appreciated that the aqueous medium fed to the further fermenter or fermenters from the first fermenter may contain some residual quantity of the limiting nutrient and/or the addition of a further small quantity thereof may be desirable for efficient operation.

Alternatively the fermentation may be conducted as a single stage continuous process. In order to achieve polyester accumulation by means of nutrient limitation the residence time of the medium in the fermenter is made sufficiently long to allow the micro-organism to grow and exhaust the limiting nutrient supplied to the fermenter and to allow the micro-organism then to accumulate the polyester.

In either a batch process, or continuous processes as described above, the acid (or derivative thereof) used to provide the copolymer repeat units II is used as part, or all, of the substrate during the polymer accumulation stage occurring upon exhaustion of the nutrient required for growth. The comonomer component may be used in admixture with a substrate, e.g. a carbohydrate, that will give repeat units I, or may be the sole substrate: in the latter case sufficient of the comonomer component will normally be metabolised by other pathways to acetyl CoA to provide the repeat units I and any acetyl CoA required to produce the repeat units II, e.g. if a pathway involving reaction 2a, is employed. However, when the comonomer component is the sole substrate, the yield of polymer is often low.

The comonomer component may be present for only part of the polymer accumulation stage: for the rest of the polymer accumulation stage, which may occur before and/or after the part of the polymer accumulation stage wherein the comonomer component is present, a substrate giving only repeat units I may be the sole substrate.

In some cases it may be possible to prevent the "normal" metabolism of the comonomer component, i.e. to acetyl CoA, by blocking enzymes required for that pathway and/or by using micro-organisms that lack the ability to synthesise the necessary enzymes. However in order to obtain substantial yields of polymer a period of cultivation under conditions of limitation, and preferably depletion, of a nutrient required for growth is generally desirable.

The fermentation is preferably conducted so that the amount of accumulated polyester comprises about 50 to 80% by weight of the bacterial cells.

Micro-organisms that may be used include any poly(3-hydroxybutyrate accumulating micro-organism that are capable of assimilating the acid (or derivative thereof) from which it is desired to produce the copolymers. The bacteria *Alcaligenes eutrophus* (previously known as *Hydrogenomonas eutropha*) species, e.g. strain H 16 widely employed in academic studies of this species, see e.g. J General Microbiology (1979) 115 pages 185-192, and which is available as ATCC strain 17699, and mutants of strain H 16 such as mutants 11/7B, S301/C5, S501/C29 and S501/C41, which have been deposited, on Aug. 18, 1980 with the National Collection of Industrial Bacteria, Torry Research Station, Aberdeen, Scotland, under NCIB Nos. 11600, 11599, 11597 and 11598 respectively, are particularly suitable. The ATCC number refers to the number designated by the American Type Culture Collection, 12301 Park Lawn Drive, Rockville, Md. 20852, U.S.A. As mentioned hereinbefore a carbohydrate is preferably used as the substrate during the growth stage. While *Alcaligenes eutrophus* strain H 16 (ATCC 17699) will not utilise glucose, certain mutants thereof, e.g. the aforesaid mutants 11/7B, S301/C5, S501/C29 and S501/C41 can utilise glucose. Carbohydrates, particularly glucose, are the preferred substrates for the growth stage in view of the cost and the fact that the micro-organisms can grow efficiently thereon.

The polyester is produced as granules inside the micro-organism cells. While the cells containing the polyester may themselves be used as a moulding material, for example as described in U.S. Pat. No. 3,107,172, it is generally desirable to separate the polyester from the bacterial cells. This may be accomplished by subjecting the cells to a cell breakage step followed by extraction of the polyester with a suitable solvent. Examples of suitable extraction processes are described in our European patent application No. 15123.

As mentioned hereinbefore the copolymers should have a weight average molecular weight (Mw) above 10,000 as measured by gel permeation chromatography, if they are to be of any practical use. Preferably Mw is above 50,000, more preferably above 100,000 and in particular above 200,000.

The copolymers invariably have the D-configuration and exhibit melting points below that of the 3-hydroxybutyrate homopolymer.

The copolymers are of particular utility in the preparation of melt-fabricated articles, where their reduced crystallinity compared to 3-hydroxybutyrate homopolymer is often advantageous.

Of particular interest is the use of small amounts of the copolymers as high molecular weight processing aids for vinyl chloride polymers. For this application the amount of copolymer is preferably 0.5 to 10% by weight of the vinyl chloride polymer. For the best results in this application, we have found that the copolymer should be random: to obtain random copolymers, the comonomer component used to produce the comonomer units II is preferably the sole substrate present, at least throughout the period of cultivation of the micro-organism under the conditions of polymer accumulation.

Copolymers are also of particular utility in the production of film by melt extrusion, preferably followed by rolling, e.g. passage through one or more pairs of rolls, to reduce the film thickness and induce some orientation, at a temperature between the glass transition temperature (Tg) and the melting point of the polymer.

The invention is illustrated by the following examples.

EXAMPLE 1

In the normal metabolism of propionate, the latter is converted, as described hereinbefore, to succinate which can give rise to acetyl CoA by oxidation in the TCA cycle to oxaloacetic acid followed by decarboxylation. In the decarboxylation of oxaloacetic acid both terminal acid groups are removed as carbon dioxide. Hence if propionate having the carbon atom of the carboxyl group radio labelled, i.e. 1-$^{14}$C- propionate, is supplied to the cells conversion to acetyl CoA will result in loss of the radioactivity as $^{14}CO_2$. Any incorporation of $^{14}C$ into the polymer must result from conversion of propionyl CoA into 3-hydroxyvaleryl CoA and subsequent polymerisation.

*Alcaligenes eutrophus* mutant NCIB 11599 was grown by aerobic cultivation in a batch fermenter employing an aqueous medium A which contained sufficient assimilable nitrogen to support a biomass free of accumulated polyester of 3.5 g $1^{-1}$ and glucose as the substrate. Medium A had the composition, per liter of deionised water:

$(NH_4)_2SO_4$: 2 g
$MgSO_4.7H_2O$: 0.8 g
$K_2SO_4$: 0.45 g
$H_3PO_4$(1.1M): 12 ml
$FeSO_4.7H_2O$: 15 mg
Trace element solution: 24 ml The trace element solution had the following composition, per liter of de-ionised water $CuSO_4.5H_2O$: 0.02 g
$ZnSO_4.6H_2O$: 0.1 g
$MnSO_4.4H_2O$: 0.1 g
$CaCl_2.2H_2O$: 2.6 g When the biomass concentration reached 4.5 g $1^{-1}$, i.e. after the system became starved of assimilable nitrogen, 1 g $1^{-1}$ of sodium propionate containing 1-$^{14}$C- propionate was added to the fermenter in addition to glucose and fermentation continued for 5 minutes. The cells were then harvested by filtration and the polymer extracted with chloroform. The labelled carbon was found almost exclusively in the chloroform solution indicating that the labelled terminal carbon atom had not been lost as carbon dioxide. Hence at least some propionate had been incorporated into the polymer other than as acetyl CoA.

EXAMPLE 2. (Comparative)

*Alcaligenes eutrophus* mutant MCIB 11599 was grown by aerobic cultivation at pH 6.8 and 34° C. in a 5 liter batch fermenter containing 4000 ml of an aqueous medium B having the composition, per liter of deionised water:

$(NH_4)_2SO_4$: 4 g
$MgSO_4.7H_2O$: 0.8 g
$K_2SO_4$: 0.45 g
$H_3PO_4$(1.1M): 12 ml
$FeSO_4.7H_2O$: 15 mg
Trace element solution (as used in Example 1) 24 ml Glucose was fed to the fermenter at a rate of 8 g hr$^{-1}$. The amount of assimilable nitrogen in medium B was sufficient to support 26 g of PHB-free cells.

After 40 hours the cells were harvested by centrifugation; they were then freeze dried and the polymer extracted with chloroform.

EXAMPLE 3

Example 2 was repeated except that when the cell weight reached 34 g, propionic acid was fed to the fermenter instead of glucose at a rate of 2.8 g hr$^{-1}$.

EXAMPLE 4

Example 3 was repeated except that feed of propionic acid was commenced when the cell weight reached 39 g.

EXAMPLE 5

Example 3 was repeated except that the feed of propionic acid was commenced when the cell weight reached 56 g.

EXAMPLE 6

Example 3 was repeated except when the cell weight reached 48 g of single addition of 12 g of propionic acid was made.

EXAMPLE 7

Example 2 was repeated except that medium A was used and propionic acid was fed at a rate of 4 g hr$^{-1}$ instead of glucose throughout the fermentation.

EXAMPLE 8

Example 2 was repeated except that when the cell weight reached 38 g, a mixture of glucose and propionic acid was fed to the fermenter, instead of glucose, at a rate of 5.2 g hr$^{-1}$ glucose and 2.8 g hr$^{-1}$ propionic acid.

EXAMPLE 9

Example 8 was repeated except that the mixture of glucose and propionic acid was fed at a rate of 6.8 g hr$^{-1}$ glucose and 1.2 g hr$^{-1}$ propionic acid, commencing when the cell weight reached 28 g.

In Examples 2 to 9 the propionic acid was added as a solution containing 400 g$^{-1}$.

EXAMPLE 10

Example 2 was repeated except that when the cell weight reached 28 g, isobutyric acid was fed to the fermentation vessel at a rate of 2 g hr$^{-1}$ in place of glucose. The isobutyric acid was added as a solution containing 150 g l$^{-1}$.

In Examples 3–6 and 8–10 the fermentations were continued until the ratio of the weight of acid fed to the fermenter to the sum of the weight of glucose fed to the fermenter after the cell weight had reached 26 g, i.e. when the system became nitrogen depleted, and the weight of acid fed to the fermenter, reached the values set out in Table 1.

EXAMPLE 11

Example 2 was repeated except that when the cell weight reached 26.4 g, 3-chloropropionic acid was fed to the fermenter instead of glucose at a rate of 4 g hr$^{-1}$ for 5 hours.

EXAMPLE 12

Example 11 was repeated except that feed of 3-chloropropionic acid was commenced when the cell weight reached 34.4 g.

EXAMPLE 13

Example 12 was repeated except that a single addition of 4 g of 3-chloropropionic was made when the cell weight reached 30 g and then glucose was fed at a rate of 6.8 g hr$^{-1}$ for 7 hours.

In Examples 11–13 the 3-chloropropionic acid was added as a solution containing 50 g l$^{-1}$.

EXAMPLE 14

Example 2 was repeated except that when the cell weight reached 31 g, acrylic acid was fed to the fermenter at a rate of 4 g hr$^{-1}$ for 5 hours instead of glucose. The acrylic acid was fed as a solution containing 100 g l$^{-1}$.

TABLE 1

| Example | Acid | Acid feed ratio* (%) | Final cell concentration (g.l$^{-1}$) | Amount of Polymer in cells. (% by weight) |
|---|---|---|---|---|
| 2 | none | 0 | 20.0 | 70 |
| 3 | propionic | 75 | 15.6 | 70 |
| 4 | propionic | 50 | 13.3 | 60 |
| 5 | propionic | 33 | 16.0 | 70 |
| 6 | propionic | 4 | 13.0 | 63 |
| 7 | propionic | 100 | 6.4 | 55 |
| 8 | propionic | 17 | 13.6 | 55 |
| 9 | propionic | 9.5 | 14.2 | 67 |
| 10 | isobutyric | 66 | 13.0 | 50 |
| 11 | 3-chloropropionic | 61 | 7.4 | 25 |
| 12 | 3-chloropropionic | 33 | 4.5 | 20 |
| 13 | 3-chloropropionic | 6.5 | 9.3 | 35 |
| 14 | acrylic | 50 | 6.0 | 25 |

*acid feed ratio is defined as the weight of acid fed to the fermenter divided by the sum of the weight of glucose added after the cell dry weight reached 26 g and the weight of acid fed to the fermenter, said ratio being expressed as a percentage.

The amount of comonomer units in the polymers of Examples 2 to 14 was determined (a) by methanolysis and gas chromatography and (b) by $^{13}$C nuclear magnetic resonance spectroscopy.

The molecular weights of the polymers were determined by gel permeation chromatography.

Chlorine analyses were also performed on the polymers of Examples 2, 11, 12 and 13.

The results are shown in Table 2.

In the table 3-HV indicates 3-hydroxyvalerate units while the units A are those mentioned hereinbefore and which are believed to be 3-hydroxypropionate units.

It is seen that little of the chlorine from 3-chloropropionic acid is to be found in the polymer. It would therefore appear that during the metabolism of 3-chloropropionic acid, chlorine is replaced and the resulting product metabolised to give the units A and the 3-hydroxyvalerate units. However, the chlorine content of the polymers of Examples 11–13 may indicate that some of the chlorine is present as chlorine containing groups R in the units II, possibly as $R^1$=chloroethyl and $R^2=R^3=R^4$=H, n=1.

TABLE 2

| Example | Acid employed | Units II found | Mole % units II by NMR | Mole % units II by methanolysis and gas chromatography | Molecular weight Mw × 10⁻³ | Molecular weight Mw/Mn | chlorine ppm. |
|---|---|---|---|---|---|---|---|
| 2 | none | none | 0 | 0 | 292 | 2.75 | 40 |
| 3 | propionic | 3-HV | 27 | 33 | 207 | 4.23 | |
| 4 | propionic | 3-HV | 24 | 27 | 374 | 1.89 | |
| 5 | propionic | 3-HV | 13 | 14 | 258 | 3.50 | |
| 6 | propionic | 3-HV | 6 | 3 | 348 | 1.66 | |
| 7 | propionic | 3-HV | 25 | 26 | 336 | 1.70 | |
| 8 | propionic | 3-HV | 15 | 14 | 389 | 1.67 | |
| 9 | propionic | 3-HV | 6 | 7 | 243 | 2.56 | |
| 10 | isobutyric | 3-HV | 30 | 29 | 274 | 2.38 | |
| 11 | 3-chloropropionic | 3-HV | 7 | — | | | |
| | | A | 1.8 | — | 383 | 2.99 | 475 |
| 12 | 3-chloropropionic | 3-HV | 4 | — | | | |
| | | A | 1.2 | — | 376 | 1.77 | 265 |
| 13 | 3-chloropropionic | 3-HV | 2 | — | | | |
| | | A | 0.6 | — | 311 | 1.99 | 45 |
| 14 | acrylic | 3-HV | 1 | — | | | |
| | | A | 6.5 | — | 353 | 2.36 | |

High resolution $^{13}$C NMR was used to investigate the monomer sequences of the copolymers of Examples 3-10. The signal derived from the carbon atom of the carbonyl group was found to occur at different chemical shifts depending upon its environment. Thus with polymers containing the units I and II (where n=1, $R^1=C_2H_5$, $R^2=R^3=R^4=H$) the possible sequences are A. butyrate-butyrate, i.e.

B. valerate-valerate, i.e.

C. butyrate-valerate, i.e.

NMR examination of the polymers of Examples 2-10 revealed three resonances occurring at 169.07, 169.25 and 169.44 ppm respectively. Following the work of M. Iida et al (Macromolecules 11, 1978, p 490) the resonance at 169.07 ppm can be assigned to the butyrate-butyrate sequence A, and that at 169.44 ppm to the valerate-valerate sequence B. By inference the signal at 169.25 must arise from the butyrate-valerate sequence C.

Quantitative analysis of the NMR results of the copolymer of example 10 gave the following results:
sequence A (butyrate-butyrate): 55%
sequence B (valerate-valerate): 14%
sequence C (butyrate-valerate): 31%

These results clearly indicate that the polymer of Example 10 contains a substantial amount of a copolymer of units I and II (where n=1, $R^1=C_2H_5$, $R^2=R^3=R^4=H$). However it is possible that some homopolymer of repeat unit I is also present.

All the polymers of Examples 2-14 had the D(−) configuration.

The melting behaviours of the copolymers as extracted was first determined by differential scanning calorimetry (DSC) using the Dupont 1090 system with computerised data analysis. DSC was also performed on the samples after compression moulding at 190° C. and slow cooling in the press in order to obtain a fully crystallised product. In each case the specimens were heated at 20° C./min in air and the temperatures at the start (Ts) and peak (Tp) of the melting endotherm, together with its area, were noted. Heating of the annealed sample was continued to 200° C. and, after isotherming for one minute to ensure complete melting, it was quenched in liquid nitrogen. The DSC was then re-run in order to determine the glass transition temperature (Tg) of the amorphous phase. Finally the densities of the annealed copolymers were measured by flotation in a density gradient.

The results are shown in Table 3.

TABLE 3

| Example | DSC on extracted polymer Ts °C. | DSC on extracted polymer Tp °C. | DSC on extracted polymer Area J·g⁻¹ | DSC on annealed polymer Tg °C. | DSC on annealed polymer Ts °C. | DSC on annealed polymer Tp °C. | DSC on annealed polymer Area J·g⁻¹ | Density g·cm⁻³ |
|---|---|---|---|---|---|---|---|---|
| 2 | 140 | 183 | 100 | 5.9 | 140 | 191 | 127 | 1.256 |
| 3 | 120 | 125 | 5 | −1.9 | 140 | 171 | 18 | 1.172 |
| | | 166 | 20 | | | | | |
| 4 | 120 | 170 | 50 | 0.8 | 140 | 182 | 44 | 1.174 |
| 5 | 110 | 120 | 5 | 2.2 | 140 | 177 | 45 | 1.200 |
| | | 170 | 50 | | | | | |
| 6 | 120 | 172 | 100 | 2.7 | 120 | 173 | 96 | 1.225 |
| 7 | 80 | 132 | 34 | 0.4 | 80 | 132 | 40 | 1.198 |
| 8 | 110 | 120 | 6 | 2.0 | 140 | 174 | 43 | 1.199 |
| | | 166 | 60 | | | | | |
| 9 | 110 | 156 | 89 | 4.0 | 110 | 163 | 81 | 1.210 |
| 10 | 50 | 65 | 10 | −2.0 | 130 | 172 | 26 | 1.138 |
| | | 168 | 25 | | | | | |
| 11 | 110 | 170 | 57 | 5.0 | 120 | 180 | 73 | — |
| 12 | 110 | 177 | 86 | 4.1 | 120 | 173 | 86 | 1.182 |
| 13 | 100 | 172 | 98 | 5.9 | 120 | 171 | 96 | 1.218 |
| 14 | 110 | 172 | 84 | 2.7 | 110 | 174 | 75 | 1.212 |

The wide melting ranges of the copolymers indicated that the copolymers were of rather heterogeneous composition. However significant randomisation by ester interchange occurred on annealing since the melting endotherms became much sharper and slightly reduced in area. This is indicative that the polymers are not physical blends of homopolymers but are genuine copolymers.

Multiple DSC peaks were observed for the "as extracted" polymers of Examples 3, 5, 8 and 10.

The area of the melting endotherms gives an indication of the degree of crystallinity. All the polymers of Examples 3 to 14 after annealing were significantly less crystalline than the control homopolymer of Example 2.

EXAMPLE 15

*Alcaligenes eutrophus* mutant NCIB 11599 was grown by aerobic cultivation at pH 6.8 and 34° C. in a 5 liter batch fermenter containing 4000 ml of an aqueous medium C which was the same as medium B except that the amount of ammonium sulphate was 5.2 g $l^{-1}$ which is sufficient to support 8.5 g $l^{-1}$ of PHB-free cells.

The substrate was glucose supplied at a rate of 5.5 g $l^{-1}hr^{-1}$. When the cell concentration reached 7 g $l^{-1}$, propionic acid was fed at a rate of 1.58 g $l^{-1}$ in addition to the glucose. The cells were harvested when the call dry weight reached 15 g $l^{-1}$. The cell suspension was spray dried, lipids extracted by refluxing the dried cells with methanol, and the polymer then extracted by refluxing with chloroform. The polymer was recovered by precipitation by adding the chloroform solution to a methanol/water mixture.

The copolymer contained 20 mole % of repeat units II where $R^1$ was ethyl, $R^2$, $R^3$, $R^4$ were each hydrogen, and n=1. The copolymer had a molecular weight of 350,000, and was insoluble in cold methyl ethyl ketone. When 2 g of the copolymer was refluxed with 100 ml of methyl ethyl ketone for 1 hour it all dissolved: on cooling the solution a gelatinous mass was formed. In contrast less than 0.1 g of a 3-hydroxybuytrate homopolymer dissolved when 2 g of the homopolymer was refluxed with 100 ml of methyl ethyl ketone. When these solubility tests were repeated with ethanol in place of methyl ethyl ketone, about 0.7 g of the copolymer, and less than 0.04 g of the homopolymer, had dissolved after refluxing for 1 hour.

The solubility of the copolymer in ethanol was also assessed at a lower concentration: thus 0.5 g of the copolymer was refluxed with 1 liter of ethanol for 1 hour. Less than 0.2 g of the copolymer dissolved.

In contrast it is noted that the polymers described by Wallen et al in "Environmental Science and Technology" 8 (1974) pages 576–579 were said to be soluble in hot ethanol.

EXAMPLE 16

Aqueous media D, E, and F were made up to the following compositions, per liter of deionised water:

Medium D $(NH_4)_2SO_4$: 12 g
$MgSO_4.7H_2O$: 1.2 g
$K_2SO_4$: 1.5 g
$CaCl_2$: 0.12 g
$FeSO_4.7H_2O$: 0.1 g
$ZnSO_4.7H_2O$: 0.006 g
$MnSO_4.4H_2O$: 0.006 g
$CuSO_4.5H_2O$: 0.0015 g
$H_2SO_4$ (concentrated): 1 ml

Medium E $H_3PO_4(1.1M)$: 2.4 ml
glucose: 40 g

Medium F $H_3PO_4(1.1M)$: 2.4 ml
propionic acid: 40 g

A sterilised batch fermenter of nominal capacity 250 liters was filled to the 130 liter mark with a mixture of approximately equal volumes of media D and E. A small sample of the medium in the fermenter was then analysed for nitrogen content. The fermenter was then inoculated with *Alcaligenes eutrophus* mutant NCIB 11599 and fermentation conduction aerobically at 34° C. with automatic pH control at 6.8 by addition of a sodium hydroxide solution.

The amount of assimilable nitrogen present in the fermenter was sufficient to support the growth of the micro-organism to only about 1.2 kg of polymer-free cells. When the cell weight reached about 1.05 kg feed of medium E was commenced at a rate of 6.5 liters/hour.

When the weight of cells reached approximately 1700 g feed of medium E was stopped and feed of medium F commenced at a rate of 6.5 liters/hour, and fermentation continued until about 2.6 kg of cells had been produced.

The cell suspension was then concentrated by centrifugation to a concentration of about 60 g/liter and the polymer extracted therefrom by contacting 1 volume of the suspension with 2 volumes of 1,2-dichloroethane (DCE) in a Silverson mixer at 20° C. for 15 minutes. The DCE phase was separated from the aqueous phase, which contained the cell debris, and filtered. The polymer was precipitated by adding 1 volume of the filtered DCE phase to 4 volumes of a methanol/water mixture (4 volumes of methanol to 1 volume of water). The precipitated polymer was collected by filtration, washed with methanol, and dried in an oven for 4 hours at 100° C.

The polymer had a melting range, as determined by differential scanning calorimetry, of about 100° C. to 180° C. with a peak in the melting endotherm at 168° C.

EXAMPLE 17

The fermentation procedure of Example 16 was repeated except that the changeover from feeding medium E to feeding medium F took place when the weight of cells was approximately 3.5 kg. The medium F was fed at a rate of 11.4 liters/hour for 4 hours and then reduced to 3.2 liters/hour and maintained at this level for a further 9 hours at which stage the weight of cells was about 3.9 kg.

In this example the amount of assimilable nitrogen present in the fermenter was sufficient to support the growth of the micro-organism to only about 1.5 kg of polymer-free cells.

The cell suspension was concentrated by centrifugation and then the polymer was extracted from the concentrated cell suspension by the procedure described in Example 15.

EXAMPLE 18

A 250 liter fermenter was charged and inoculated as in Example 16. The amount of assimilable nitrogen was sufficient to support growth of the micro-organisms only to about 1.9 kg of polymer-free cells. As in Example 16 fermentation was conducted aerobically at 34° C. at a pH of 6.8.

When the cell weight reached about 1.0 kg feeds of medium E and of a medium G at rates of 8.7 liters/hour and 4.6 liters/hour respectively were commenced and continued until the cell weight reached about 3.9 kg.

Medium G had the composition, per liter of deionised water:

H$_3$PO$_4$(1.1M): 1.2 ml
propionic acid: 20 g

The cell suspension was concentrated by centrifugation and then the polymer extracted from the concentrated cell suspension by the procedure described in Example 15.

EXAMPLE 19

The procedure of Example 17 was repeated on a larger scale using a fermenter of nominal capacity 1000 liters which was filled to the 500 liter mark with approximately equal volumes of media D and E. In this example the feed of medium E was commenced, at a rate of 25 liters/hour, when the weight of cells was about 4 kg and the feed of medium F was commenced, at a rate of 37.5 liters/hour, when the weight of the cells was about 8 kg. The feeds of media E and F were continued until the weight of cells was about 10 kg. The amount of assimilable nitrogen present was sufficient to support the growth of the micro-organism to only about 4.1 kg of polymer-free cells.

EXAMPLE 20

Example 19 was repeated except that the feed rate of medium F was 25 liters/hour and the fermentation was continued until the weight of the cells was about 11 kg. In this case the amount of assimilable nitrogen present was sufficient to support the growth of the micro-organism to only about 4 kg of polymer-free cells.

The polymers of Examples 16–20 were each copolymers containing 3-hydroxybutyrate (HB) units and 3-hydroxyvalerate (HV) units, and had weight average molecular weights above 300,000. They each had the D(−) configuration.

100 parts by weight of each of the polymers of Examples 16–20, and of a 3-hydroxybutyrate homopolymer were slurried with about 10 parts by weight of chloroform and 1 part by weight of Steamic talc, and granulated at room temperature through a domestic mincer. The compositions were then dried to remove the chloroform and extruded at 190° C. and regranulated. The resulting granules were injection moulded at 185° C. into test bars using a mould temperature of 60° C. and a cooling time of 20 sec. The tensile properties were measured according to ASTM D 638-77a at a rate of 50 mm/min and the impact strength assessed by the Izod impact test according to ASTM D 256-78.

The results are shown in Table 4.

TABLE 4

| Example | HV/HB molar ratio by GC | HV/HB molar ratio by NMR | Modulus* (GPa) | Tensile Strength (MPa) | Extension to Break (%) | Izod Impact strength (J/m) 1 mm notch | Izod Impact strength (J/m) unnotched |
|---|---|---|---|---|---|---|---|
| 16 | 18/82 | 20/80 | 1.47 | 25 | 10–31 | 66 | 463 |
| 17 | 4/96 | 6/94 | 2.98 | 33 | 5–7 | 23 | 140 |
| 18 | 8/92 | 7/93 | 2.10 | 31 | 14–19 | 106 | 408 |
| 19 | 1/99 | 4/96 | 2.70 | 35 | 8–14 | 56 | 191 |
| 20 | 4/96 | 4/96 | 2.48 | 35 | 8–15 | 23 | 140 |
| homo-polymer | 0/100 | 0/100 | 3.25 | 40 | 6–13 | 65 | 115 |

*at 0.5% extension

EXAMPLE 21

A PVC formulation was made by dry blending the following ingredients at room temperature:

| | | parts by weight |
|---|---|---|
| (i) | vinyl chloride homopolymer (K62) | 100 |
| (ii) | a complex tin thiooctyl stabiliser based on di-N—dithioglycollic acid ester | 1.5 |
| (iii) | methyl methacrylate/butadiene/styrene PVC impact modifier | 8 |
| (iv) | wax (external lubricant) | 0.8 |
| (v) | glyceryl monoester (internal lubricant) | 1 |
| (vi) | HB polymer (processing aid) | 2 |

The HB polymer processing aids were
(a) a 3-hydroxybutyrate homopolymer prepared by the procedure of Example 2
(b) the copolymer of Example 7 (copolymer A)
(c) the copolymer of Example 16 (copolymer B)

The processing aids were slurried with about 10% by weight of chloroform, granulated at room temperature through a domestic mincer, dried, melt extruded at 190° C., regranulated, and ground to a particle size below 150 μm before incorporation into the PVC dry blend.

The dry blends were tested as follows:
1. 50 g of the mixture was poured into the mixing head of a Brabender Plastograph maintained at 180° C. rotating at 18 rpm under a pressure ram loaded with a 5 kg weight. The time taken for gelation to occur was measured.
2. The mixture was cold compressed to form a candle which was then charged to an extrusion rheometer maintained at 170° C. and fitted with a die having a circular orifice of 1 mm diameter and 20 mm land length. After the charge had heated to 170° C., it was extruded at increasing rates. The appearance of the extrudate was noted and the melt extensibility assessed by attempting to draw the extrudate away from the die. The results are shown in Table 5.

TABLE 5

| Processing aid | Gelation time (min) at 180° C. | Extrusion at 170° C. Appearance | Melt extensibility |
|---|---|---|---|
| None | 12 | Severe sharkskin at low extrusion rates; ripple at higher rates | Poor |
| homopolymer | 9.5 | Poor with a lot of unmelted polymer clearly visible | Poor |
| copolymer A | 1.0 | Excellent - very smooth | Good |
| copolymer B | 1.5 | Smooth, but occasional unmelted particles | Fair |

This example shows that the copolymers are superior to 3-hydroxybutyrate homopolymer as a vinyl chloride polymer processing aid. The more random copolymer A was clearly superior to the copolymer B.

EXAMPLE 22

A medium H was made up to the following composition:
- (NH₄)₂SO₄: 1 g
- KH₂PO₄: 2 g
- (Na)₂HPO₄: 3 g
- MgSO₄.7H₂O: 0.2 g
- CaCl₂: 0.01 g
- FeSO₄.7H₂O: 0.005 g
- MnSO₄.4H₂O: 0.002 g
- Na₂CO₃.10H₂O: 0.1 g
- (NH₂)₂CO: 1.5 g
- deionised water—to 1 liter This medium had a pH of 7.

Eight 1 liter shake flasks each containing 500 ml of medium H, in which 0.5 g of methacrylic acid had been dissolved, were each inoculated with 5 ml of a starter culture of *Nocardia salmonicolor* strain ATCC 19149 and incubated at 32° C. on a gyratory shaker.

0.5 g of methacrylic acid was added to each flask at intervals of 24, 48 and 72 hours after inoculation, and a final addition of 0.25 g of methacrylic acid was made 96 hours after inoculation. After a total of 108 hours after inoculation the flasks were examined: little or no growth of the microorganism was apparent in any of the flasks. The contents of the flasks were combined and centrifuged to give a pellet of cells which was dried in an oven and weighed. The weight of the pellet was 2.81 g. The cell content of the inoculum was also determined and found to be 69.75 g.l⁻¹: Hence the total weight of cells added, as the inoculum, to the flasks was 2.79 g.

It is concluded that, at the concentrations of methacrylic acid employed, this strain does not assimilate methacrylic acid.

EXAMPLES 23-45

In these examples a range of acids and derivatives thereof were screened for their ability to give copolymers.

The technique employed was as follows: *Alcaligenes eutrophus* mutant NCIB 11599 was grown by aerobic cultivation at pH 6.8 and 34° C. in a 5 liter batch fermenter containing 3500 to 4000 ml of an aqueous medium having the composition, per liter of de-ionised water:
- glucose: 17 g
- (NH₄)₂SO₄: 4 g
- MgSO₄.7H₂O: 0.8 g
- H₃PO₄(1.1M): 12 ml
- FeSO₄.7H₂O: 15 mg Trace element solution (as used in Example 1): 36 ml
The pH was controlled at 6.8 by the automatic addition of a 9:1 v/v mixtures of 4M potassium hydroxide and 4M sodium hydroxide. This addition of a KOH/NaOH mixture to control pH also served to supply potassium and sodium to the cultivation medium.

The amount of assimilable nitrogen (provided by the 4 g/l of ammonium sulphate) was sufficient to support only about 6.5 g/l of HB polymer-free cells. As about 16 g/l of glucose are required to produce 6.5 g/l of HB polymer free cells, the amount of glucose present was sufficient to provide a small carbon excess. By monitoring the residual glucose concentration and also the dissolved oxygen tension trace, a clear indication was obtained when the system became starved of assimilable nitrogen. At this stage feed of the comonomer component, i.e. the acid or derivative under study, was commenced and continued until a total of about 0.1 to 5 g/l of the comonomer component had been added.

After completion of the addition of the comonomer component, the cells were harvested by centrifugation. A sample of the centrifuged cells was freeze dried and the polymer was extracted with chloroform. The polymer was analysed by a gas chromatography/mass spectroscopy (GCMS) technique (which involves a preliminary transesterification step) or by nuclear magnetic resonance spectroscopy (NMR).

The results are shown in table 6. In this table the NMR results are quoted where possible as these are considered to be the more definitive since the NMR technique does not involve a transesterification step.

TABLE 6

| | Comonomer component | | |
|---|---|---|---|
| Example | nature | period over which comonomer component added (hr) | total amount added (g/l) | Units II found |
| 23 | propionic acid | 5 | 5 | 3-HV |
| 24 | ethyl propionate | 1.75 | 2.5 | 3-HV* |
| 25 | 3-hydroxypropionic acid | 1 | 1 | 3-HV and "A" |
| 26 | 3-hydroxypropionic acid | 16.5 | 3.4 | 3-HV and "A" |
| 27 | 2-chloropropionic acid | 0.5 | 0.3 | none |
| 28 | 3-chloropropionic acid | 0.5 | 0.3 | 3-HV and "A" |
| 29 | 3-ethoxypropionic acid | 1 | 1 | 3-HV* |
| 30 | isobutyric acid | 5 | 5 | 3-HV |
| 31 | 2-chlorobutyric acid | 0.5 | 0.3 | none |
| 32 | 2-hydroxybutyric acid | 0.5 | 1 | 3-HV |
| 33 | 4-hydroxybutyric acid | 3 | 2 | none |
| 34 | phenyl acetic acid | 2 | 2 | none |
| 35 | 2-chloroacetic acid | 3.5 | 0.3 | none |
| 36 | acrylic acid | 5 | 3.5 | 3-HV and "A" |
| 37 | 2-methylacrylic | 0.5 | 1 | none |

TABLE 6-continued

| | Comonomer component | | | |
|---|---|---|---|---|
| Example | nature | period over which comonomer component added (hr) | total amount added (g/l) | Units II found |
| | acid | | | |
| 38 | 2,3-dimethyl-acrylic acid | 0.5 | 1 | none |
| 39 | 3,3-dimethyl-acrylic acid | 1 | 1 | none |
| 40 | glyoxylic | 5 | 2 | none |
| 41 | glycolic | 3 | 2 | none |
| 42 | lactic | 5.5 | 3 | none* |
| 43 | benzoic | 24 | 5 | none* |
| 44 | formic | 4 | 2 | none |
| 45 | valeric | 4 | 2.5 | 3-HV*+ |

*Only GCMS analysis performed.
+polymer contained about 33% 3-HV units.

Similar results were obtained when Examples 23–44 were repeated using an alternative cultivation regime wherein a mixture of glucose and the comonomer component was continuously added after nitrogen starvation had been attained.

EXAMPLES 46–51

*Alcaligenes eutrophus* mutant NCIB 11599 was grown by continuous aerobic cultivation at pH 6.8 and 34° C. in a 5 liter fermenter with a working volume of about 4 liters at a dilution ratio (reciprocal of residence time) of 0.085 hr$^{-1}$. The aqueous medium employed had the following composition, per liter of deionised water:

MgSO$_4$.7H$_2$O: 0.8 g
K$_2$SO$_4$: 0.45 g
Na$_2$SO$_4$: 0.05 g
H$_3$PO$_4$(1.1M): 12 ml
Trace element solution (as used in Example 1): 36 ml The ingredients set out in Table 7 were also continuously supplied to the fermenter.

TABLE 7

| Ingredient | Amount added per liter of medium in the fermenter | Supplied as a solution containing, per liter of deionised water |
|---|---|---|
| Fe | 5 mg | 2 g FeSO$_4$ · 7H$_2$O<br>1 ml conc. H$_2$SO$_4$· |
| N | 850 mg | 50 g NH$_4$OH |
| Propionic acid | 26 g | 400 g propionic acid |
| acrylic acid | see Table 8 | 40 g acrylic acid |

The amount of nitrogen was sufficient to support only 6.5 g/l of HB-polymer free cells.

pH was controlled at 6.8 by the automatic addition of a 9:1 v/v mixture of 4M potassium hydroxide and 4M sodium hydroxide.

Fermentation was commenced using propionic acid as the sole substrate. 3 days after steady state conditions had been achieved a sample of the aqueous cell suspension product was taken and then acrylic acid was added as a cosubstrate in increasing amounts. Prior to each increase in acrylic acid concentration a sample of the aqueous cell suspension product was taken. Fermentation under steady state conditions for at least 3 days was performed at each acrylic acid concentration before taking each sample. Each sample of the aqueous cell suspension product was centrifuged to harvest the cells which were then freeze dried. The polymer was extracted from the cells with chloroform and then analysed by NMR.

The results are shown in Table 8.

TABLE 8

| Example | Amount of acrylic acid added, per liter of medium in the fermenter (g) | Cell dry weight g/l | Polymer content (% by weight) | NMR analysis (mole %) | | |
|---|---|---|---|---|---|---|
| | | | | 3-HB | 3-HV | other |
| 46 | 0 | 11.9 | 45 | 70 | 30 | 0 |
| 47 | 0.25 | 11.8 | 45 | 70 | 19 | 11 (units A) |
| 48 | 0.5 | 10.8 | 40 | 72 | 20 | 8 (units A) |
| 49 | 1.0 | 10.5 | 38 | 81 | 19 | 0 |
| 50 | 2.0 | 9.3 | 30 | 90 | 10 | 0 |
| 51 | 4.5 | 7.1 | 9 | 89 | 11 | 0 |

EXAMPLE 52

In this example *Alcaligenes eutrophus* mutant NCIB 11599 is grown aerobically at 34° C. in under phorphorus, rather than nitrogen, limitation. A 5 liter fermenter was charged with 3 liters of an aqueous medium containing, per liter of deionised water:

(NH$_4$)$_2$SO$_4$: 6.2 g
H$_3$PO$_4$(1.1M): 1.5 ml
MgSO$_4$.7H$_2$O: 0.8 g
FeSO$_4$.7H$_2$O: 15 mg
Trace element solution (as used in Example 1): 36 ml Fermentation was controlled at pH 6.8 automatically by the addition of a 9:1 v/v mixture of 4M KOH and 4M NaOH. The amount of phosphorus was sufficient to support only about 8 g/l of HB polymer-free cells.

The fermenter was inoculated with a 48 hr shake flask culture and then 5 g/l of glucose was added. When all the glucose had been utilised (at which stage the cell concentration was about 2.5 g/l), propionic acid was added, as a solution containing 300 g/l propionic acid) at a rate of 0.8 g/l/hr for 54 hours.

The cells were then harvested, the polymer extracted with chloroform, and analysed by CGMS. The results were as follows:

Final cell concentration: 20 g/l
Polymer content: 60%
mole % 3-HV: 40%

EXAMPLES 53–57

In these Examples two strains of *Nocardia salmonicolor* were grown on glucose and then polymer accumulation induced using various acids.

In each example a 250 ml shake flask was charged with 50 ml of an aqueous medium containing, per liter of deionised water glucose: 10 g
K₂HPO₄: 1.9 g
NaH₂PO₄: 1.56 g
(NH₄)₂ SO₄: 1.8 g
MgSO₄.7H₂O: 0.2 g
FeCl₃.6H₂O: 0.001 g
Trace element solution (as used in Example 1): 1 ml The pH of the aqueous medium was 7.0. The flask was inoculated with the organism and grown, with gyratory shaking, at 30° C. for 24 hours. The resultant suspension was then centrifuged and the supernatant aqueous medium discarded. The centrifuged pellet was then resuspended in 50 ml of an aqueous medium identical to that above except that the 10 g/l of glucose was replaced by 1 g/l of the acid and the 1.8 g/l of ammonium sulphate was omitted. The resuspended cells were shaken for a further 24 hours at 30° C. and then the cell suspension centrifuged. The centrifuged pellet of cells was washed twice with methanol and analysed for polymer content. The polymer was analysed by GCMS. The results are shown in Table 9.

TABLE 9

| Example | N. salmonicolor strain | acid | approx. polymer content (% by weight) | GCMS mole % 3-HB | 3-HV |
|---|---|---|---|---|---|
| 53 | ATCC 19149 | isobutyric | 10 | 35 | 65 |
| 54 | ATCC 19149 | 2-chloropropionic | 12 | 63 | 37 |
| 55 | ATCC 21243 | propionic | 10 | 38 | 72 |
| 56 | ATCC 21243 | isobutyric | 10 | 30 | 70 |
| 57 | ATCC 21243 | 2-chloropropionic | 12 | 38 | 62 |

We claim:

1. Copolymers having a weight average molecular weight above 10,000 and containing repeat units

—O.CH(CH₃).CH₂.CO—  I and repeat units

—O.CR¹R².(CR³R⁴)ₙ.CO—  II where n is 0 or an integer and R¹, R², R³, and R⁴ are each selected from hydrocarbon radicals: halo- and hydroxy-substituted hydrocarbon radicals; hydroxy radicals; halogen atoms; and hydrogen atoms, provided that, where n is 1 and R², R³, and R⁴ are each hydrogen atoms, R¹ is not methyl, said repeat units II constituting 0.1 to 50 mole % of the total repeat units in said copolymer.

2. Copolymers according to claim 1 wherein n is 1.
3. Copolymers according to claim 1 wherein R¹, R², R³ and R⁴ each contain less than 4 carbon atoms.
4. Copolymers according to claim 1 wherein at least one of R¹, R², R³ and R⁴ is hydrogen.
5. Copolymers according to claim 4 wherein R², R³ and R⁴ are each hydrogen.
6. Copolymers according to claim 5 containing repeat units

—O.CH(CH₃).CH₂.CO—  I and repeat units

—O.CH(C₂H₅).CH₂.CO—  II

7. Copolymers according to claim 5 containing repeat units —O.CH(CH₃).CH₂.CO— together with repeat units —O.CH₂.CH₂.CO— alone or in conjunction with repeat units —O.CH(C₂H₅)CH₂.CO—.

8. Copolymers according to claim 1 containing 1 to 40 mole % of repeat units II.

9. Copolymers having a weight average molecular weight above 10,000 and containing at least 50 mol % of repeat units

—O.CH(CH₃)CH₂.CO— and being characterised by a triplet at 4.3 ppm as measured by proton nuclear magnetic resonance spectroscopy and peaks at 59.89 and 33.83 ppm (relative to a tetramethyl silane standard) measured by ¹³C nuclear magnetic resonance spectroscopy.

10. Copolymers according to claim 1 having a weight average molecular weight above 200,000.

11. A process for the production of a thermoplastic polyester wherein a micro-organism that is capable of accumulating a polyester is cultivated in an aqueous medium on a water soluble assimilable carbon containing substrate with at least part of the cultivation being conducted under conditions such that the micro-organism accumulates at least 10% by weight of polyester, characterised in that, at least during part of the period when polyester is being accumulated, the substrate comprises an organic acid, or derivative thereof, that is metabolisable by said micro-organism under said polyester accumulating conditions to a polyester other than one composed solely of —O.CH(CH₃).CH₂.CO— repeat units, the amount the combined carbon in said acid, or derivative thereof, constituting at least 2% by weight of the total combined carbon in the substrate present throughout said period.

12. A process according to claim 11 wherein the acid is selected from propionic, isobutyric, and acrylic acid.

13. A process according to claim 11, wherein the acid is the sole substrate for at least part of the period during which the cultivation of the micro-organism is conducted under conditions causing polyester to be accumulated.

14. A process according to claim 13 wherein the acid is the sole substrate throughout the cultivation of the micro-organism.

15. A process according to claim 11 wherein the micro-organism is grown using a carbohydrate as a substrate.

16. A process according to claim 15 wherein the carbohydrate is glucose.

17. A process according to claim 15 wherein, for at least part of the period when the cultivation is under conditions causing polyester accumulation, the substrate is a mixture of the acid and the carbohydrate.

18. A process according to claim 11 wherein the micro-organism is caused to accumulate polyester by cultivation under conditions of limitation of one or more of the essential requirements for microbial growth but not polyester accumulation.

19. A process according to claim 18 wherein the essential requirement for growth, but not polyester accumulation, that is limited, is the nitrogen source, or the phosphorus source.

20. A process according to claim 11 wherein the acid, or derivative thereof, that is metabolisable to a polyester other than one composed solely of —O.CH(CH$_3$).CH$_2$.CO— units, is the sole organic acid, or derivative thereof, present during the period when polyester is being accumulated.

21. Cells of a poly(hydroxybutyrate)-accumulating micro-organism containing at least 10% by weight of said polyester wherein said polyester comprises a copolymer as claimed in claim 1.

* * * * *